(12) United States Patent
Goldman (10) Patent No.: US 7,700,364 B2
(45) Date of Patent: Apr. 20, 2010

(54) ANALYSIS OF AMINO ACIDS IN BODY FLUID BY LIQUID CHROMATOGRAPHY-MASS SPECTROMETRY

(75) Inventor: Scott Goldman, Laguna Niguel, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 995 days.

(21) Appl. No.: 10/963,442

(22) Filed: Oct. 12, 2004

(65) Prior Publication Data

US 2007/0218561 A1 Sep. 20, 2007

(51) Int. Cl.
G01N 33/00 (2006.01)

(52) U.S. Cl. ........................................................ 436/89
(58) Field of Classification Search .................... 436/89
See application file for complete search history.

(56) References Cited

U.S. PATENT DOCUMENTS

| 5,534,440 | A | | 7/1996 | Aebersold et al. |
| 5,559,038 | A | * | 9/1996 | Kolhouse et al. ............... 436/86 |
| 5,885,841 | A | | 3/1999 | Higgs, Jr. et al. |
| 6,692,971 | B2 | | 2/2004 | Shushan et al. |
| 7,122,377 | B2 | | 10/2006 | Qiu et al. |
| 2003/0153007 | A1 | | 8/2003 | Chen et al. |

FOREIGN PATENT DOCUMENTS

WO    WO03/027681 A2 * 4/2003

OTHER PUBLICATIONS

Aebersold, R; Mann, M. "Mass Spectrometry-based proteomics." Nature, 2003, vol. 422, 198-207.*
Iida, T.; Matsunaga, H.; Fukushima, T.; Santa, T.; Homma, H.; Imai, K. "Complete Enantiomeric Separation of Phenylthiocarbamoylated Aminoa Acids on a Tandem Column of Reversed and Chiral Stationary Phases." Anal. Chem. 69, (21), pp. 4463-4468).*
Carey, F.A. "Organic Chemistry." 1992, Mc-Graw-HIll, Inc. p. 1111.*
Webarchive.org. Archive Date: Aug. 6, 2003. Phenomenex.com EZFaast Prodcut OVerview and Amino Acid Analysis pp. 286-292.*
Soga, T.; Heiger, D. N. "Amino Acid Analysis by Capillary Electrophoresis Electrospray Ionization Mass Spectroscopy." Anal. Chem. 2000, 72, 6, pp. 1236-1241.*
Kramarenko, G.G.; Markova, E.D.; Ivanova-Smolenskaya, I.A.; Boldyrev, A.A. "Pecularities of Carnosine Metabolism in a Patient with Pronouced Homocarnosinemia." Bulletin of Experimental Biology and Medicine. 2001, 132, 4, pp. 996-999.*

(Continued)

*Primary Examiner*—Walter D Griffin
*Assistant Examiner*—Bobby Ramdhanie
(74) *Attorney, Agent, or Firm*—Foley & Lardner LLP (57) ABSTRACT

A method for detecting amino acids in body fluids is described. The method includes derivatizing the body fluid amino acids (e.g. plasma amino acids), separating the derivatized amino acids by liquid chromatography followed by and subjecting the identification by mass spectrometry. The identity of each amino acid from the body fluid is determined by comparing to a set of structurally similar amino acid standards, which preferably are added to the body fluid sample as internal standards. Use of the method of diagnose an individual with a metabolic disorder is also provided.

40 Claims, 2 Drawing Sheets

OTHER PUBLICATIONS

Andrensek et al., "Determination of phenylalanine and tyrosine by liquid chromatography/mass spectrometry." Journal of AOAC International, 86:753-758, 2003.

Bures et al., "Synthesis of the protein-sequencing reagent 4-(3-Pyridinylmethylaminocarboxypropyl) phenyl Isothiocyanate and characterization of 4-(3-Pyridinylmethylaminocarboxypropyl) Phenylthiohydantoins." Analytical Biochemistry, 224:364-372, 1995.

Casetta et al. "Development of a method for rapid quantitation of amino acids by liquid chromatrography, tandem mass spectrometry (LC-MSMS) in plasma" Clin Chem lab Med (2000) 38: 391-401.

Hess et al, "Acid hydrolysis of silk fibroins and determination of the enrichment of isotopically labeled amino acids using precolumn derivitization and high performance liquid chromatography-electrspray ionization mass spectrometry" Anal Biochem (2002) 311:19-26.

Hess et al., "Liquid chromatography-electrospray ionization mass spectrometry of 4-(3-Pyridinylmethylaminocarboxypropyl)phenylthiohydantoins." Analytical Biochemistry, 224:373-381, 1995.

Hess et al., "Chirality determination of unusual amino acids using precolumn derivatization and liquid chromatography-electrospray ionization mass spectrometry." Journal of Chromatography, 1035:211-219, 2004.

Ji et al., "Determination of phenethyl isothiocyanate in human plasma and urine by ammonia derivatization and liquid chromatography-tandem mass spectrometry" Anal Biochem 323:39-47, 2003.

Lee et al., "Highly informative proteome analysis by combining improved N-terminal sulfonation for de novo peptide sequencing and online capillary reverse-phase liquid chromatography/tandem mass spectrometry." Proteomics, 4:1684-1694, 2004.

Liu et al. "Derivitization of amino acids with N,N-dimethyl-2,4-dinitro-5-fluorobenzylamine for liquid chromatography/electrospray ionization mass spectrometry" Rapid Commun Mass Spectrom 18:1059-65, 2004.

Perwaiz et al., "Determination of bile acids in biological fluids by liquid chromatography-electrospray tandem mass spectrometry." Journal of Lipid Research, 42:114-119, 2001.

Van Eijik et al., "Determination of amino acid isotope enrichment using liquid chromatography-mass spectrometry" Anal Biochem 271:8-17, 1999.

Guan et al., A simultaneous liquid chromatography/mass spectrometric assay of glutathione, cysteine, homocysteine and their disulfides in biological samples, J. Pharm. Biomed. Anal., 31:251-261 (2003).

Martens-Lobenhoffer, J. and Bode-Böger, S.M., Simultaneous detection of arginine, asymmetric dimethylarginine, symmetric dimethylarginine and citrulline in human plasma and urine aplying liquid chromatography-mass spectrometry with very straightforward sample preparation, J. Chrom. B, 798:231-239 (2003).

International Search Report for PCT Patent Application No. PCT/US2008/068653.

Bartolucci et al., Liquid chromatography tandem mass spectrometric quantitation of sulfamethazine and its metabolites: direct analysis of swine urine by triple quadrupole and by ion trap mass spectrometry. Rapid Communications in Mass Spectrometry, 14: 967-973, 2000.

Abbas et al, S-Sulfo-Cysteine is an Endogenous Amino Acid in Neonatal Rat Brain but an Unlikely Mediator of Cysteine Neurotoxicity, Neurochem Res, 33:301-307 (2008).

Annual Report ERNDIM-EQAS 2007.

Biochrom 30 Amino Acid System, product brochure available at http://www.biochrom.co.uk/download/6/Biochrom%2030%20Amino%20Acid%20Analyser%20Brochure.pdf.

Coloso, et al., Metabolism of Cyst(e)ine in Rat Enterocytes, J. Nutrition (1989), 119:1914-1924.

Description of Service Schedule and Guidelines for Sample Shipment, Medical Genetics Program, Duke University Medical Center (2008), available at http://medgenetics.pediatrics.duke.edu/wysiwyg/downloads/Mass_Spec_Sample_and_Shipping_Info_091208a.pdf.

Green, Plasma Amino Acids in a Paitent with Wilson's Disease Presenting with an Acute Haemolytic Anaemia, J. Inher. Metab. Dis. 4 (1981), pp. 33-36.

Henderson, Amino Acid Pot Pourri, Department of Clinical Biology at St. James 19s University Hospital, available at http://www.metbio.net/docs/MetBio-Presentation-KABU556300-13-06-2009.pdf.

Hernanz et al, Increased Plasma Levels of Homocysteine and Other Thiol Compounds in Rheumatoid Arthritis Women, Clinical Biochemistry, vol. 32, No. 1, pp. 65-70 (1999).

Lee et al, Plasma Amino Acid Levels in Patients with Colorectal Cancers and Liver Cirrhosis with Hepatocellular Carcinoma, Hepato-Gastroenterology, 2003, 50:1269-1273.

Li et al., CE and CE/MS for natural products, Agilent Technologies, Mar. 1, 2009.

Moyano et al, Plasma amino acids in anorexia nervosa, European Journal of Clinical Nutrition (1998), 52:684-689.

Nakamura et al, Increased Plasma Gluconeogenic and System A Amino Acids in Patients with Pancreatic Diabetes due to Chronic Pancreastitis in Comparision with Primary Diabetes, Tohoku J. Exp. Med, 1994, 173:413-420.

Parvy, et al., A New Pitfall in Plasma Amino Acid Analysis, Clinical Chem. (1989), vol. 35, No. 1, p. 178.

Ruffin et al., Column chromatography of cysteinesulfinic acid, cysteic acid, and S-sulfocysteine, Anal. Biochem. (1976), 76:233-238, Abstract.

Schmid et al, Effect of Somatostatin on Skin Lesions and Concentrations of Plasma Amino Acids in a Patient with Glucagonamoa-Syndrome, Hepato-gastroenterol. 35 (1988), pp. 34-37.

Staedt et al, Effects of ornithine aspartate on plasma ammonia and plasma amino acids in patients with cirrhosis. A double-blind, randomized study using a four-fold crossover design, Journal of Hepatology, 1993, 19:424-430.

Sigma-Adrich, Product Detail for C2196—L-Cystein S-sulfate, available at http://www.sigmaaldrich.com/catalog/ProductDetail.do?D7=0&N5=SEARCH_Contact (2009).

* cited by examiner

Table 1. Table showing various amino acids detected and quantitated by the method described herein.

| #Analyte | Analyte •=split peak | MW | PITC | AA(MW)+PITC (derivatization) | RetTime | Ions Obs'd |
|---|---|---|---|---|---|---|
| 18 | Phophoserine | 185.1 | 135.19 | 320.29 | 2.648 | 319,639 |
| 1 | Aspartic Acid | 133.1 | 135.19 | 268.29 | 2.822 | 267 |
| 2 | Glutamic Acid | 147.13 | 135.19 | 282.32 | 3.200 | 281 |
| 42 | Arginosuccinic Acid | 290.3 | 135.19 | 425.49 | 3.448 | 424,849 |
| 19 | L-alpha-aminoadipic Acid | 161.2 | 135.19 | 296.39 | 4.004 | 295 |
| 20 | Hydroxy-L-Proline | 131.1 | 135.19 | 266.29 | 4.586 | 265,531 |
| 22 | Asparagine | 132.12 | 135.19 | 267.31 | 5.489 | 266,533 |
| 3 | Serine | 105.09 | 135.19 | 240.28 | 5.703 | 239,479 |
| 23 | Glutamine | 146.1 | 135.19 | 281.29 | 6.129 | 280 |
| 4 | Glycine | 75.07 | 135.19 | 210.26 | 6.333 | 209,419 |
| 24 | Beta-Alanine | 89.09 | 135.19 | 224.28 | 6.902 | 223,447 |
| 25 | Sarcosine (Sarc) | 89.09 | 135.19 | 224.28 | 6.943 | 223 |
| 26 | Taurine | 125.1 | 135.19 | 260.29 | 7.311 | 259,519 |
| 5 | Histidine | 155.16 | 135.19 | 290.35 | 7.444 | 289,579 |
| 27 | Citrulline | 175.2 | 135.19 | 310.39 | 7.643 | 309,619 |
| 33 | GABA | 103.1 | 135.19 | 238.29 | 8.140 | 237,475 |
| 8 | Arginine | 174.2 | 135.19 | 309.39 | 8.714 | 308,617 |
| 6 | Threonine | 119.12 | 135.19 | 254.31 | 8.735 | 253,507 |
| 34 | Carnosine | 226.2 | 135.19 | 361.39 | 8.892 | 360,721 |
| 28 | DL-Beta-Aminoisobutyric Acid | 103.1 | 135.19 | 238.29 | 9.425 | 237,475 |
| 7 | Alanine | 89.09 | 135.19 | 224.28 | 9.449 | 223,447 |
| 39 | DL(+)-Allo-Gamma-Hydroxylysine | 162.2 | 135.19 | 297.39 | 10.373 | 295 |
| 9 | Proline | 115.13 | 135.19 | 250.32 | 10.514 | 249 |
| 36 | L-3-Methylhistidine | 169.2 | 135.19 | 304.39 | 10.773 | 303,607 |
| 37 | Anserine | 240.26 | 135.19 | 375.45 | 10.980 | 374,749 |
| 35 | L-1-Methylhistidine | 169.2 | 135.19 | 304.39 | 11.346 | 303,607 |
| 38 | Ethanolamine | 61.08 | 135.19 | 196.27 | 11.923 | 195 |
| 44 | L-Cysteine | 121.2 | 135.19 | 256.39 | 12.489 | 255,511 wk |
| 29 | L-alpha-Amino-N-Butyric Acid | 103.1 | 135.19 | 238.29 | 12.513 | 237,475 |
| 43 | E-Amino-n-Caproic Acid | 131.2 | 135.19 | 266.39 | 12.796 | 265,531 |
| 10 | Tyrosine | 181.19 | 135.19 | 316.38 | 13.692 | 315,631 |
| 30 | DL-Allo-Cystathionine• | 222.3 | 135.19 | 357.49 | 15.200 | 491 |
| 11 | Valine | 117.15 | 135.19 | 252.34 | 15.639 | 251,503 |
| 12 | Methionine | 149.21 | 135.19 | 284.4 | 15.728 | 283,567 |
| 13 | Cystine• | 240.3 | 135.19 | 375.49 | 16.000 | 509 |
| 14 | Isoleucine | 131.17 | 135.19 | 266.36 | 18.606 | 265,531 |
| 41 | L-allo-Ile | 131.2 | 135.19 | 266.39 | 18.713 | 265,531 |
| 15 | Leucine | 131.17 | 135.19 | 266.36 | 18.741 | 265,531 |
| 40 | Ornithine | 132.16 | 135.19 | 267.35 | 18.878 | 401,803 |
| 32 | Tryptophan | 204.23 | 135.19 | 339.42 | 18.896 | 338,677 |
| 16 | Phenylalanine | 165.19 | 135.19 | 300.38 | 19.112 | 299,599 |
| 17 | Lysine | 146.19 | 135.19 | 281.38 | 19.338 | 415,831 |
| 31 | Homocystine | 135.2 | 135.19 | 270.39 | 20.052 | 269 |
| 21 | Phosphoethanolamine (PEA) | 141.1 | 135.19 | 276.29 | | |

ANALYSIS OF AMINO ACIDS IN BODY FLUID BY LIQUID CHROMATOGRAPHY-MASS SPECTROMETRY

BACKGROUND

The present method relates generally to the field of analysis of biological fluids. In particular, the method relates to the analysis of amino acids in biological fluids.

The identity and amount of amino acids in a patient's body fluid (e.g., plasma) is important in a patient's health for a number of reasons. Aberrant amino acid levels can be used to diagnose disease or illness. For example, low plasma amino acid levels may occur in patients with cancer, anorexia, arthritis, folliculitis, alcohol abuse, glucagonoma, and/or pregnancy. Patients undergoing stress or depression may also have low plasma amino acid levels. In particular, depressed patients may be deficient in phenylalanine, tyrosine, methionine, glycine, tryptophan, and/or taurine. Psychotic patients may have low levels of amino acids such as glycine, tryptophan, and/or histidine and elevated levels of amino acids such as phenylalanine, tyrosine, and/or serine.

Patients with infectious disease and/or fever also may have reduced amino acid levels, although some amino acids in such patients such as phenylalanine may be present at elevated levels. Patients with kidney failure may have low levels of amino acids such as tyrosine, threonine, leucine, isoleucine, valine, lysine, and/or histidine. Patients with Crohn's disease, ulcerative colitis, chronic fatigue syndrome may have abnormally low levels of cystine and glutamine in their plasma.

In addition, amino acid levels that are higher than normal may be indicative of a disease state. For example, elevated plasma amino acid levels may be observed in patients with liver disease, pancreatitis, heavy metal poisoning, vitamin C deficiency, and/or vitamin D deficiency. In particular, patients with Wilson's disease may exhibit elevated levels of tryptophan and histidine. Patients with Cushing's disease or gout may exhibit elevated alanine levels. Diabetic patients may exhibit elevated levels of valine, leucine, and/or isoleucine. Hyperactive children may exhibit elevated levels of tyrosine and phenylalanine. Patients with Maple Syrup Urine Disease may have elevated levels of leucine, isoleucine, and valine in their plasma. As such, methods for analyzing amino acids in body fluids such as plasma are useful in medicinal and scientific settings.

Traditionally, analytical methods for amino acids have included a derivatization step. During derivatization, the amino acid is reacted with a derivatizing reagent that facilitates analysis of amino acids in the sample. Derivatizing agents typically react with the free amino groups of amino acids in the sample. Common reagents for derivatizing amino acids include isothiocyanates (e.g., phenyl isothiocynate (PITC)), o-phthaldialdehyde (OPA), 2,4-dinitrofluorobenzene (DNFB), and Nα-(2,4-dinitro-5-fluorophenyl)-L-alainamide (FDAA). Derivatizing agents are useful because they may include substituents that facilitate analysis of the derivatized amino acid. For example, derivatizing agents may include chromophores for UV-absorption detection or fluorophores for fluorescent detection.

Derivatized amino acids may be separated and detected by performing chromatography such as liquid chromatography (LC) or gas chromatography (GC)), coupled with mass spectrometry (i.e., LC-MS or GC-MS). Amino acids, however, have diverse chemical structures (e.g., basic, acidic, aromatic, polar, non-polar, etc.), and because of significant differences in the chemical structures of various amino acids that may be present in body fluids, these compounds present a difficult task for analysts to solve in regard to derivatization/separation in LC-MS or GC-MS.

Methods for detecting amino acids using LC and MS have been reported and include, for example, Casetta et al. "Development of a method for rapid quantitation of amino acids by liquid chromatography, tandem mass spectrometry" (LC-MSMS) in plasma" Clin Chem lab Med (2000) 38: 391-401; Hess et al, "Acid hydrolysis of silk fibroins and determination of the enrichment of isotopically labeled amino acids using precolumn derivatization and high performance liquid chromatography electrospray ionization mass spectrometry" Anal Biochem (2002) 311:19-26; Ji et al., "Determination of phenethyl isothiocyanate in human plasma and urine by ammonia derivatization and liquid chromatography-tandem mass spectrometry" Anal Biochem (2003) 323:39-47; Van Lijik et al., "Determination of amino acid isotope enrichment using liquid chromatography-mass spectrometry" (1999) Anal Biochem 271:8-17; and Liu et al. "Derivatization of amino acids with N,N-dimethyl-2,4-dinitro-5-fluorobenzylamine for liquid chromatography/electrospray ionization mass spectrometry" (2004) Rapid Commun Mass Spectrom 18:1059-65. Improved methods for detecting amino acids in body fluids is desirable.

SUMMARY

Disclosed are methods for detecting various amino acids that may be present in a body fluid of an individual. In one aspect, the method involves derivatizing the body fluid amino acids, separating the derivatized amino acids by liquid chromatography, (LC) subjecting the separated derivatized amino acids to mass spectrometry (MS), and using the MS analysis to identify derivatized amino acids from the body fluid by comparison to structurally similar amino acids from a set of amino acid standards. Structurally similar amino acids share significant structural characteristics such as key functional groups such that the identification of one amino acid by mass spectrometry can be used to identify the other structurally similar amino acid in the same method. The set of amino acid standards is preferably used as a set of internal standards by adding the set to the body fluid prior to processing.

The set of standards may be non-derivatized and added to the starting body fluid or to any post processing step prior to derivatization. In a preferred embodiment, the standards comprise deuterated amino acids. The set of standards also may be added to the body fluid amino acids after the step of derivatization. In this case, the added standards should be derivatized in the same manner as the body fluid amino acids. In one approach, the amino acids are derivatized with an isothiocyanate (e.g., phenyl isothiocynate (PITC). In a preferred embodiment, the derivatizing agent is PITC. Other suitable derivatizing agents may include o-phthaldialdehyde (OPA), 2,4-dinitrofluorobenzene (DNFB), and Nα-(2,4-dinitro-5-fluorophenyl)-L-alainamide (FDAA).

The amount of each identified amino acid from a volume of body fluid can be determined by comparing the signal by MS to the signal of a known amount of structurally similar amino acid. The amount of the amino acid in the body fluid can then be expressed relative to the volume of body fluid analyzed to obtain a concentration of the amino acid in the original body fluid. Quantitative analysis is preferably done with internal standards.

In some embodiments, the body fluid can be processed to obtain a fraction with an enriched concentration of amino acids prior to further analysis. In one approach, a low molecular weight fraction of the body fluid is obtained (e.g., by passing the bodily fluid through a molecular weight filter).

In one embodiment, the method may be used to detect at least 20 different amino acids. In other embodiments, the method may be used to detect at least 25, 30, 35, or 40 amino acids.

For example, the method may be useful for detecting and/or quantitating any combination of the amino acids including, but not limited to, phosphoserine, sulfo-cysteine, arginosuccinic acid, hydroxyproline, aspartic acid, asparagine, glutamic acid, serine, phosphoethanolamine, glutamine, glycine, histidine, sarcosine, taurine, carnosine, citrulline, arginine, anserine, 1,3-methyl-histidine, alpha-amino-adipic acid, threonine, beta-alanine, proline, ethanolamine, gamma-amino-butyric acid, beta-amino-isobutyric acid, alpha-amino-butyric acid, cysteine, tyrosine, valine, methionine, L-allo-cystathionine (cystathionine-A), L-cystathionine (cystathionine-B), cystine, isoleucine, allo-isoleucine, leucine, DL-hydroxylysine (hydroxylysine (1)), DL-allo-hydroxylysine (hydroxylysine (2)), phenylalanine, ornithine, tryptophan, homocystine, and lysine. In addition, the method may be used to diagnose a disease state based on the level of any of the detected amino acids in plasma.

In one embodiment, the method may be useful for detecting and/or quantitating any combination of the amino acids including, but not limited to, phosphoserine, sulfo-cysteine, arginosuccinic acid, hydroxyproline, aspartic acid, phosphoethanolamine, sarcosine, carnosine, anserine, 1,3-methyl-histidine, alpha-amino-adipic acid, beta-alanine, proline, ethanolamine, gamma-amino-butyric acid, beta-amino-isobutyric acid, cysteine, L-allo-cystathionine-A, L-cystathionine, cystine, allo-isoleucine, DL-hydroxylysine, DL-allo-hydroxylysine, and homocystine.

In another embodiment, the method may be useful for detecting and/or quantitating any combination of the amino acids including, but not limited to, phosphoserine, sulfo-cysteine, arginosuccinic acid, hydroxyproline, aspartic acid, phosphoethanolamine, sarcosine, carnosine, anserine, 1,3-methyl-histidine, alpha-amino-adipic acid, beta-alanine, proline, ethanolamine, gamma-amino-butyric acid, beta-amino-isobutyric acid, cysteine, L-allo-cystathionine-A, L-cystathionine, cystine, DL-hydroxylysine, DL-allo-hydroxylysine, and homocystine. In a further embodiment, the method can be used to identify any of cysteine, phosphoserine or arginosuccinic acid.

In a further embodiment, the method may be useful for detecting and/or quantitating any combination of the amino acids including, but not limited to, phosphoserine, sulfo-cysteine, arginosuccinic acid, hydroxyproline, phosphoethanolamine, sarcosine, carnosine, anserine, 1,3-methyl-histidine, alpha-amino-adipic acid, beta-alanine, proline, ethanolamine, gamma-amino-butyric acid, beta-amino-isobutyric acid, cysteine, L-allo-cystathionine-A, L-cystathionine, cystine, allo-isoleucine, DL-hydroxylysine, DL-allo-hydroxylysine, and homocystine.

In a further embodiment, the method may be useful for detecting and/or quantitating any combination of the amino acids including, but not limited to, phosphoserine, sulfo-cysteine, arginosuccinic acid, hydroxyproline, phosphoethanolamine, sarcosine, carnosine, anserine, 1,3-methyl-histidine, alpha-amino-adipic acid, ethanolamine, gamma-amino-butyric acid, beta-amino-isobutyric acid, L-allo-cystathionine-A, L-cystathionine, cystine, allo-isoleucine, DL-hydroxylysine, DL-allo-hydroxylysine, and homocystine.

In a further embodiment, the method may be useful for detecting and/or quantitating any combination of the amino acids including, but not limited to, phosphoserine, cysteine, arginosuccinic acid, hydroxyproline, phosphoethanolamine, sarcosine, carnosine, anserine, 1,3-methyl-histidine, alpha-amino-adipic acid, ethanolamine, gamma-amino-butyric acid, beta-amino-isobutyric acid, L-allo-cystathionine-A, L-cystathionine, cystine, DL-hydroxylysine, DL-allo-hydroxylysine, and homocystine.

LC separation of derivatized amino acids may be performed using any type of LC system such as are commercially available. A suitable LC column is one that has a packing material which includes minute particles (e.g., silica particles having a diameter of about 2-5 μm, and preferably about 3 μm). The particles typically have pores of about 50 to 300 angstroms, and preferably about 150 angstroms. The particles typically have a surface area of about 50-600 $m^2/g$, and preferably about 100 $m^2/g$.

The particles may include a hydrophobic stationery phase bonded to their surface. In one embodiment, the hydrophobic stationery phase may be an alkyl phase, which may include C-4, C-8, and C-18 (preferably C-18).

The column may have any suitable dimensions. Preferably, the column has a diameter of about 0.5 mm to about 5 mm and a length of about 15 mm to about 300 mm, and most preferably, a diameter of about 2 mm and a length of about 50 mm.

LC separation of derivatized amino acids may also be performed using a hydrophobic solvent or a solvent mixture that includes a hydrophobic solvent in a gradient as a mobile phase to elute the amino acids. In one embodiment, the derivatized fraction may be applied to the column in an aqueous buffer (i.e., a hydrophilic solvent) and the amino acids may be eluted by applying a mobile phase to the column that has an increasing amount of organic solvent (i.e., a hydrophobic solvent). For example, the aqueous buffer may include (95% $H_2O$, 5% acetonitrile), and the amino acids may be eluted from the column by gradually increasing the concentration of acetonitrile to about 100% in the mobile phase. If desirable, the mobile phase may be heated to a temperature of about 40-60° C., preferably about 50° C. In addition, the mobile phase may optionally include one or more additional reagents that are useful during LC and/or MS. For example, ammonium acetate or acetic acid.

MS analysis of derivatized amino acids may be performed by ionization of the sample. Suitable ionization techniques include electrospray ionization (ESI), atmospheric pressure chemical ionization (APCI), photoinonization, electron ionization, fast atom bombardment (FAB)/liquid secondary ionization (LSIMS), matrix assisted laser desorption ionization (MALDI), field ionization, field desorption, thermospray/plasmaspray ionization, and particle beam ionization. Preferably, MS is performed using ESI. Further, MS may be performed using a negative or positive ion mode, and preferably a negative ion mode.

MS analysis of derivatized amino acids may be performed with any of several types of ion analyzers including quadrupole analyzers, ion traps analyzers, and time-of-flight analyzers. Preferably, MS may be performed using a quadrupole analyzer. The ions generated during MS may be detected by using several detection modes including selective ion monitoring mode (SIM) and scanning mode. Preferably, the ions are detected by using SIM. MS is preferably other than tandem MS.

Also provided is a method of diagnosing the existence of a metabolic disorder involving amino acid metabolism in an individual. The method comprises determining if a body fluid contains an abnormal level of one or more amino acids by first (a) derivatizing the body fluid amino acids; (b) separating the derivatized amino acids by liquid chromatography (LC); (c) subjecting the separated derivatized amino acids to mass spectroscopic analysis (MS) using a mass spectrometer; and (d) using the MS analysis to identify the amount of derivatized amino acids from the body fluid by comparing to structurally similar amino acids from a set of amino acid standards. Various embodiments of this method are similar to those already discussed.

BRIEF DESCRIPTION OF THE FIGURES

FIG. 1 is a table showing various amino acids detected and quantitated by the methods described herein. Third column indicates MW "molecular weight"; fourth column indicates PITC molecular weight; fifth column indicates molecular weight of each PITC derivitized amino acids; six column is the LC retention time; seventh column indicates mass spectrometry ions observed.

DETAILED DESCRIPTION OF THE PREFERRED EMBODIMENTS

As used herein, "amino acid" means any molecule that includes an alpha-carbon atom covalently bonded to an amino group and an acid group. The acid group may include a carboxyl group. "Amino acid" may include molecules having one of the formulas:

wherein R is a side group and Z includes at least 3 carbon atoms. "Amino acid" includes the twenty amino acids lysine, asparagine, threonine, serine, isoleucine, methionine, proline, histidine, glutamine, arginine, glycine, aspartic acid, glutamic acid, alanine, valine, phenylalanine, leucine, tyrosine, cysteine, tryptophan, and isomers thereof (e.g., stereoisomers). "Amino acid" includes L-amino acids and D-amino acids. "Amino acid" also includes derivatives of the twenty amino acids such as phosphoserine (PSER), sulfocysteine, arginosuccinic acid (ASA), hydroxyproline, phosphoethanolamine (PEA), sarcosine (SARC), taurine (TAU), carnosine (CARN), citrulline (CIT), anserine (ANS), 1,3-methyl-histidine (ME-HIS), alpha-amino-adipic acid (AAA), beta-alanine (BALA), ethanolamine (ETN), gamma-amino-butyric acid (GABA), beta-amino-isobutyric acid (BAIA), alpha-amino-butyric acid (BABA), L-allo-cystathionine (cystathionine-A; CYSTA-A), L-cystathionine (cystathionine-B; CYSTA-B), cystine, allo-isoleucine (ALLO-ILE), DL-hydroxylysine (hydroxylysine (1)), DL-allo-hydroxylysine (hydroxylysine (2)), ornithine (ORN), and homocystine (HCY).

As used herein, "body fluid" means any fluid that can be isolated from the body of an individual. For example, "body fluid" may include blood, plasma, serum, bile, saliva, urine, tears, perspiration, and the like.

As used herein, "derivatizing" means reacting two molecules to form a new molecule. For example, an amino acid may be derivatized by reacting the amino acid with a derivatizing agent to form a derivatized amino acid. Derivatizing may include reacting the alpha amino group of the amino acid with an electrophilic atom of a derivatizing agent to form a covalent bond. Derivatizing agents may include isothiocyanate groups, dinitro-fluorophenyl groups, nitrophenoxycarbonyl groups, and/or phthalaldehyde groups.

As used herein, "liquid chromatography" (LC) means a process of selective retardation of one or more components of a fluid solution as the fluid uniformly percolates through a column of a finely divided substance, or through capillary passageways. The retardation results from the distribution of the components of the mixture between one or more stationery phases and the bulk fluid, (i.e., mobile phase), as this fluid moves countercurrent to the stationery phases. The process is used for analysis and separation of mixtures of two or more substances. "Liquid chromatography" includes reverse phase liquid chromatography (RPLC) and high pressure liquid chromatography (HPLC).

As used herein, "mass spectroscopic" analysis (MS analysis) means an analytical technique to identify unknown compounds including: (1) ionizing the compounds and potentially fractionating the compounds to form charged compounds; and (2) detecting the molecular weight of the charged compound and calculating a mass-to-charge ratio (m/z). The compound may be ionized and detected by any suitable means. A "mass spectrometer" includes means for ionizing compounds and detecting charged compounds.

As used herein, "electrospray ionization" means a technique used in mass spectrometry to ionize macromolecules and to overcome the propensity of macromolecules to fragment. In "electrospray ionization" a liquid is pushed through a very small charged metal capillary by a carrier gas. The liquid contains the substance which is to be studied, the analyte, as well as a large amount of solvent, which is usually much more volatile then the analyte. The charge contained in the capillary transfers to the liquid which charges the analyte molecule. As like charges repel, the liquid pushes itself out of the capillary and forms a mist or an aerosol of small droplets about 10 μm across, to increase the distance between the similarly charged molecules. A neutral carrier gas is used to evaporate the neutral solvent in the small droplets, this in turn brings the charged analyte molecules closer together. The proximity of the molecules becomes unstable, however, and as the similarly charges molecules come closer together, the droplets once again explode. This process repeats itself until the analyte is free of solvent and a lone ion is formed. The lone ion is transported to a mass analyzer.

As used herein, a "quadrupole analyzer" is a mass analyzer composed of quads (i.e., two pairs of metallic rods aligned in parallel), wherein one pair of rods is at a positive electrical potential and the other set of rods is at a negative potential. To be detected, an ion must pass through the center of a trajectory path bordered and parallel to the aligned rods. When the quads are operated at a given amplitude of direct current and radio frequency voltages, only ions of a given m/z ratio will resonate and have a stable trajectory to pass through the quadrupole and be detected. "Positive ion mode" means a mode wherein positively charged ions are detected by the mass analyzer. "Negative ion mode" means a mode wherein negatively charged ions are detected by the mass analyzer. For "single ion monitoring" or "selected ion monitoring" (i.e., SIM), the amplitude of the direct current and the radio frequency voltages are set to observe only a specific mass.

As used herein, a "low molecular weight fraction" is a fraction that is enriched in one or more low molecular weight molecules. A low molecular weight molecule typically has a molecular weight of less than about 1000 daltons, and more typically less than about 500 daltons.

As used herein, "hydrophobic" means not dissolving in water. "Hydrophobic" compounds include long chain alkanes. A hydrophobic solvent is a solvent that is capable of dissolving a hydrophobic compound.

As used herein "about" when used in the context of a number means the number plus or minus 10%.

Disclosed is a method for identifying and/or quantitating amino acids in a body fluid. The body fluid can be blood, plasma, serum, bile, saliva, urine, and the like. A preferred body fluid is plasma or serum.

A set of amino acid standards representing the types of amino acids that might be present in a particular body fluid is preferably added to the body fluid sample before any processing. The set of amino acid standards preferably contains a known amount of each amino acid present in the set. A set of amino acid standards may include one or more amino acids from the group consisting of lysine, asparagine, threonine, serine, isoleucine, methionine, proline, histidine, glutamine, arginine, glycine, aspartic acid, glutamic acid, alanine, valine, phenylalanine, leucine, tyrosine, cysteine, tryptophan, phosphoserine, sulfo-cysteine, arginosuccinic acid, hydroxyproline, phosphoethanolamine, sarcosine, taurine, carnosine, citrulline, anserine, 1,3-methyl-histidine, alpha-amino-adipic acid, beta-alanine, ethanolamine, gamma-amino-butyric acid, beta-amino-isobutyric acid, alpha-amino-butyric acid, L-allo-cystathionine (cystathionine-A), L-cystathionine (cystathionine-B), cystine, allo-isoleucine, leucine, DL-hydroxylysine (hydroxylysine (1)), DL-allo-hydroxylysine (hydroxylysine (2)), ornithine, tryptophan, homocystine, and isomers thereof (e.g., stereoisomers).

The amino acids of the set of amino acid standards may be modified so that they can be easily discriminated from the corresponding amino acids found in the body fluid. The internal standard amino acid preferably behaves closest to the amino acid that it is chosen to represent chemically and physically but fragments to ions of a different mass upon mass spectrometric analysis. Thus, a preferred set of amino acids standards is deuterated.

Body fluid may be processed prior to derivatization to obtain and enriched preparation of the amino acids. Various procedures may be used for this purpose depending on the type of body fluid. These include filtration, precipitation, centrifugation, combinations thereof and the like. Separation of a low molecular weight fraction is a preferred approach. Size separation on small volumes of sample is preferably performed by filtering using a low molecular weight cutoff filter. The filtered body fluid sample (i.e., permeate) will include free amino acids and the retained components (i.e., retentate) will include high molecular weight components such as proteins. Suitable filters for generating a filtrate include 45 micron, 22 micron and 100,000, 50,000 and 10,000 dalton cutoff filters. In addition, high molecular weight components may be precipitated from the plasma sample by adding alcohol (e.g., methanol) or acid to the sample. High molecular weight components may also be removed from the sample by high speed centrifugation.

Derivatization of amino acids is performed following any necessary processing of the body fluid sample. The amino acids in the sample typically are derivatized to facilitate separation and/or detection of free amino acids in the sample during LC-MS (e.g., pre-column derivatization is first performed where LC is subsequently performed). The derivatizing agent may include substituents that facilitate detection of the derivatized amino acids during or after chromatography (e.g., fluorophores or chromophores). In addition, the derivatizing agent may include substituents that facilitate ionization of the derivatized amino acids during mass spectrometry.

Typical derivatizing agents include isothiocyanates (e.g., phenyl isothiocynate (PITC)), o-phthaldialdehyde (OPA), 2,4-dinitrofluorobenzene (DNFB), and Nα-(2,4-dinitro-5-fluorophenyl)-L-alainamide (FDAA). In a preferred embodiment, the derivatizing agent is PITC.

After the amino acids in the sample have been derivatized, the sample is subjected to chromatographic separation, preferably high pressure liquid chromatographic separation, and mass spectrometry (i.e., LC-MS).

Liquid chromatography and mass spectrometry may be performed by placing the derivatized sample in an instrument that includes a chromatographic column in flow communication with a mass spectrometer. The chromatographic column typically includes a medium (i.e., a packing material) to facilitate separation of the derivatized amino acids (i.e., fractionation). The medium may include minute particles that have a diameter of approximately 2-6 μm, preferably about 3 μm. For example, the particles may be silica particles. The particles may have pores that have a diameter of approximately 50-300 angstroms, preferably 150 angstroms. Additionally, the particles may have a surface area of approximately 50-600 $m^2/g$, preferably 100 $m^2/g$.

The particles include a bonded surface that interacts with the derivatized amino acids to facilitate separation of the amino acids. One suitable bonded surface is a hydrophobic bonded surface such as an alkyl bonded surface. Alkyl bonded surfaces may include C-4, C-8, or C-18 bonded alkyl groups, preferably C-18 bonded groups.

The column may have any suitable dimensions. In particular, the column may have a diameter of about 0.5-5 mm and a length of about 15-300 mm. Preferably, the column has a diameter of about 2 mm and length of about 50 mm.

Suitable media for preparing a chromatographic column and/or prepared columns may be obtained from commercial sources. In particular, suitable columns may be obtained from Thermo Electron Corporation (e.g., 250×2.1 mm, 5 μm, BetaBasic C18 column).

The chromatographic column includes an inlet port for receiving a sample and an outlet port for discharging an effluent that includes the fractionated sample. In the method, the derivatized sample is applied to the column at the inlet port, eluted with a solvent or solvent mixture, and discharged at the outlet port. Different solvent modes may be selected for eluting the amino acids. For example, liquid chromatography may be performed using a gradient mode, an isocratic mode, or a polytyptic (i.e. mixed) mode. Preferably, liquid chromatography is performed using a gradient mode. In the gradient mode, the derivatized sample is applied to the column and a mixture of two solvents (i.e., the mobile phase) is passed through the column to elute the amino acids. Generally, as known in the art, one of the solvents will tend to be relatively hydrophilic, and the other solvent will tend to be relatively hydrophobic. As a specific example of a solvent combination found to be suitable in the practice of the present method, the hydrophilic solvent may be 95% $H_2O$, 5% acetonitrile and the hydrophobic solvent may be 100% acetonitrile. Optionally, the solvent combination may include one or more reagents to facilitate separation and/or detection of the derivatized amino acids (e.g., 20 mM ammonium acetate). Some reagents may be added to the mobile phase to improve the shape of the chromatographic peak and/or to provide a source of ions for LC-MS.

In most cases, to perform liquid chromatography with a gradient solvent, two pumps are used that mix the two solvents. Initially, as the solvents are mixed, the solvent mixture that is passed through the column (i.e., mobile phase) includes mostly hydrophilic solvent. Gradually, the amount of hydrophilic solvent in the mixture is decreased and the amount of hydrophobic solvent in the mixture is increased to create a solvent gradient. Ultimately, the solvent mixture that is passed through the column includes mostly hydrophobic solvent. In this manner, hydrophilic amino acids will be eluted before hydrophobic amino acids.

The mass spectrometer includes an inlet port for receiving the fractionated sample that is in flow communication with the outlet port of the chromatographic column. The mass spectrometer is capable of generating one or more mass spectroscopic data sets for identifying one or more amino acids in the sample. Suitable instruments for performing LC-MS may be obtained from commercial sources. In particular, suitable instruments for performing LC-MS may be obtained from Agilent Technologies (e.g., Agilent 1100 Series LC/MSD).

The mass spectrometer will include an ion source for ionizing the fractionated sample and creating charged molecules for further analysis. Ionization of the sample may be performed by electrospray ionization (ESI), atmospheric pressure chemical ionization (ACPI), photoinonization, electron ionization, fast atom bombardment (FAB)/liquid secondary ionization (LSIMS), matrix assisted laser desorption ionization (MALDI), field ionization, field desorption, thermospray/plasmaspray ionization, and particle beam ionization. Electrospray ionization is preferred.

After the sample has been ionized, the positively charged or negatively charged ions thereby created may be analyzed to determine a mass-to-charge ratio (i.e., m/z). Preferably, the negatively charged ions are analyzed. Suitable analyzers for determining mass-to-charge ratios include quadrupole analyzers, ion traps analyzers, and time-of-flight analyzers. Preferably, the mass-to-charge ratio is determined using a quadrupole analyzer. The ions may be detected by using several detection modes. For example, selected ions may be detected (i.e., using a selective ion monitoring mode (SIM)), or alternatively, ions may be detected using a scanning mode. Preferably, the ions are detected by using SIM.

Example

Serum was obtained from a patient by taking a blood sample and allowing the sample to clot. The clotted sample was then centrifuged and the serum (i.e., supernatant) was removed for analysis. Deuterated internal standards were added to about 100 μl of the serum to form a test mixture. The test mixture then was passed through a 10,000 molecular weight filter to provide a low molecular weight filtrate fraction as a test sample. The test sample was then dried under nitrogen at 40-75° C.

After the test sample was dry, the sample was dissolved in about 25 μl of a redry solution (equal volumes of methanol, 1M sodium acetate, and triethylamine). The dissolved sample was then dried under nitrogen at 40° C. After the dissolved sample was dry, the dried sample was dissolved in 50 μl of a derivatizing solution (methanol; 1.12 μl of 100%, water; 1.60 μl, triethylamine; 1.60 μl of 100%, and phenylisothiocyanate (PITC); 1.60 μl of 100%). The dissolved sample was then heated at about 40° C. for about 15-20 minutes. The dissolved sample was then dried under liquid nitrogen at 50-60° C. After the sample was dry, the dried sample was then dissolved in 100 μl of a reconstitution solution (95% $H_2O$, 5% acetonitrile). The samples were vortexed to facilitate dissolution of the dried sample and then transferred to vials for liquid chromatography (LC).

The instrument used for LC and mass spectroscopic analysis (MS) was Agilent's 1100 Series LC/MSD. To perform LC, the sample was applied to a Thermo Beta-Basic C-18 (250× 2.1 mm) HPLC column. The hydrophobic solvent used for LC was 20 mM ammonium acetate in 100% acetonitrile. The amino acids were eluted from the column using a mobile phase in a gradient mode (i.e., the mobile phase goes from 5% acetonitrile to 100% acetonitrile). The mobile phase was heated to 50° C. during the analysis.

Figure 2:
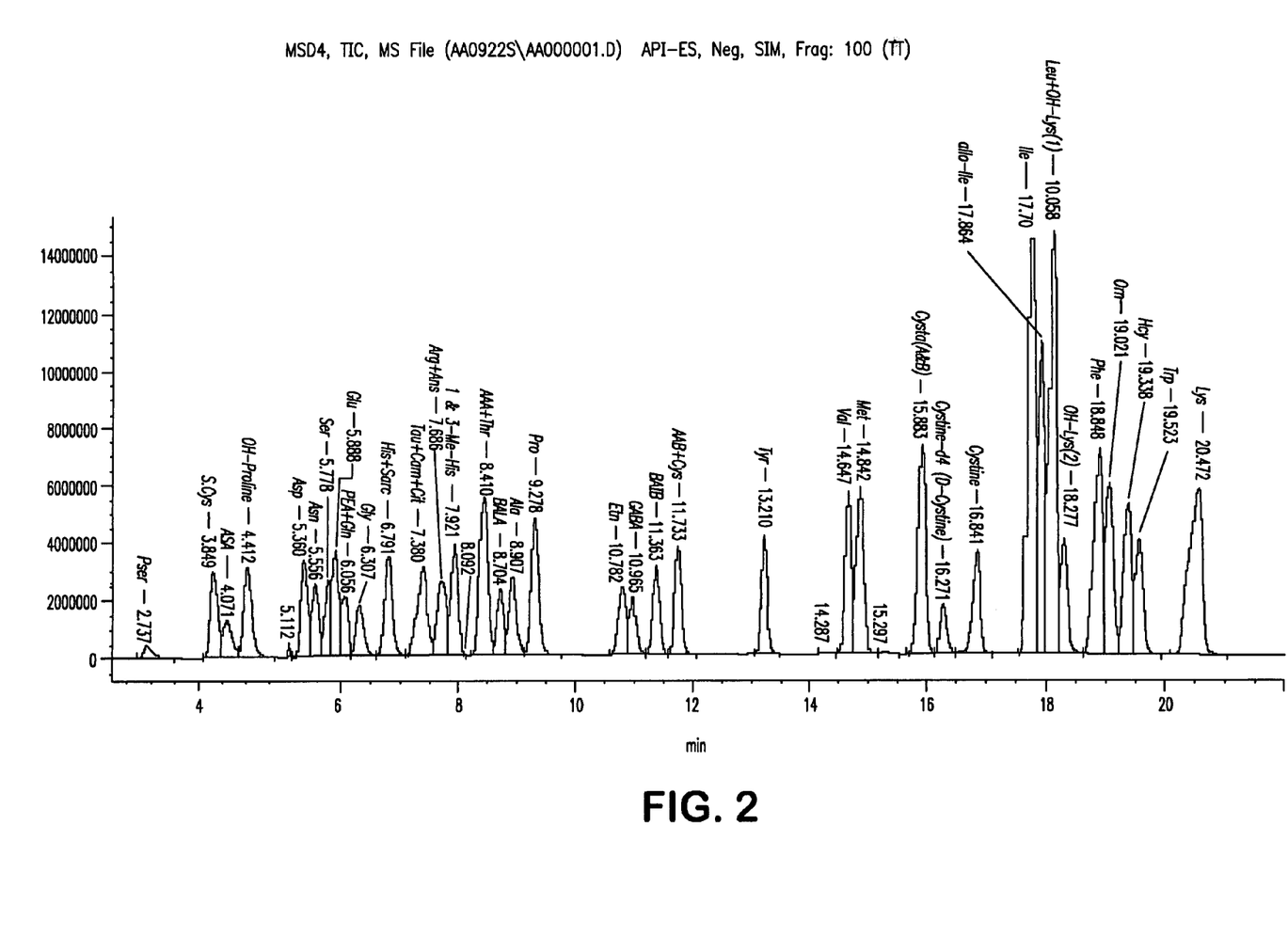
FIG. 2 shows the results of MS analysis of a single sample containing the indicated amino acids, previously subject to LC. The ion size characteristic of each amino acid is indicated.

For MS, electrospray ionization was used and the sample was analyzed in the negative mode using selective ion monitoring. Amino acids detected by the method include phosphoserine, sulfo-cysteine, arginosuccinic acid, hydroxyproline, aspartic acid, asparagine, glutamic acid, serine, phosphoethanolamine, glutamine, glycine, histidine, sarcosine, taurine, camosine, citrulline, arginine, anserine, 1,3-methyl-histidine, alpha-amino-adipic acid, threonine, beta-alanine, proline, ethanolamine, gamma-amino-butyric acid, beta-amino-isobutyric acid, alpha-amino-butyric acid, cysteine, tyrosine, valine, methionine, L-allo-cystathionine (cystathionine-A), L-cystathionine (cystathionine-B), cystine, isoleucine, allo-isoleucine, leucine, DL-hydroxylysine (hydroxylysine (1)), DL-allo-hydroxylysine (hydroxylysine (2)), phenylalanine, ornithine, tryptophan, homocystine, and lysine. FIGS. 1 and 2 list the various amino acids detected in a typical run.

What is claimed is:

1. A method for identifying the presence of one or more free amino acids in a body fluid of an individual, comprising:
   (a) derivatizing free amino acids in the body fluid;
   (b) separating the derivatized free amino acids by liquid chromatography (LC);
   (c) subjecting the separated derivatized free amino acids from step (b) to mass spectroscopic (MS) analysis using a mass spectrometer to identify derivatized free amino acids from the body fluid by comparison to structurally similar amino acids from a set of free amino acid standards, wherein the identified derivatized free amino acids include one or more free amino acids selected from the group consisting of phosphoserine, sulfocysteine, phosphoethanolamine, carnosine, anserine, 1,3-methyl-histidine, L-allo-cystathionine-A, and DL-allo-hydroxylysine, wherein said MS is other than tandem MS.

2. The method of claim 1, wherein the set of amino acid standards is added to the body fluid prior to step involving LC or the step involving MS.

3. The method of claim 1, wherein the free amino acids are derivatized with phenylisothiocyanate.

4. The method of claim 1, further comprising processing the body fluid to obtain an enriched preparation of free amino acids prior to derivatizing the free amino acids.

5. The method of claim 4, wherein the enriched preparation of free amino acids comprises a low molecular weight fraction of the body fluid.

6. The method of claim 1, further comprising the step of quantifying the amount of the one or more free amino acids detected in the body fluid.

7. The method of claim 1, wherein the body fluid is plasma.

8. The method of claim 1, wherein the set of amino acid standards comprises at least 22 free amino acids.

9. The method of claim 1, wherein the set of amino acid standards comprises at least 30 free amino acids.

10. The method of claim 1, wherein the set of amino acid standards comprises at least 35 free amino acids.

11. The method of claim 1, wherein the set of amino acid standards comprises at least 40 free amino acids.

12. The method of claim 1, wherein the set of amino acid standards comprises at least 45 free amino acids.

13. The method of claim 1, wherein the step involving MS is performed using electrospray ionization.

14. The method of claim 1, wherein the step involving MS is performed using a quadrupole analyzer.

15. The method of claim 1, wherein the identified derivatized free amino acids include one or more free amino acids selected from the group consisting of phosphoserine, sulfocysteine, arginosuccinic acid, hydroxyproline, aspartic acid, phosphoethanolamine, sarcosine, carnosine, anserine, 1,3-methyl-histidine, alpha-amino-adipic acid, beta-alanine, proline, ethanolamine, gamma-amino-butyric acid, beta-amino-isobutyric acid, cysteine, L-allo-cystathionine-A, L-cystathionine, cystine, DL-hydroxylysine, DL-allo-hydroxylysine, and homocystine.

16. The method of claim 1, wherein the identified derivatized free amino acids include one or more free amino acids selected from the group consisting of phosphoserine, sulfocysteine, arginosuccinic acid, hydroxyproline, phosphoethanolamine, sarcosine, carnosine, anserine, 1,3-methyl-histidine, alpha-amino-adipic acid, beta-alanine, proline, ethanolamine, gamma-amino-butyric acid, beta-amino-isobutyric acid, cysteine, L-allo-cystathionine-A, L-cystathionine, cystine, allo-isoleucine, DL-hydroxylysine, DL-allo-hydroxylysine, and homocystine.

17. The method of claim 1, wherein the identified derivatized free amino acids include one or more free amino acids selected from the group consisting of phosphoserine, sulfocysteine, arginosuccinic acid, hydroxyproline, phosphoethanolamine, sarcosine, carnosine, anserine, 1,3-methyl-histidine, alpha-amino-adipic acid, ethanolamine, gamma-amino-butyric acid, beta-amino-isobutyric acid, L-allo-cystathionine-A, L-cystathionine, cystine, allo-isoleucine, DL-hydroxylysine, DL-allo-hydroxylysine, and homocystine.

18. The method of claim 1, wherein the identified derivatized free amino acids include one or more free amino acids selected from the group consisting of phosphoserine, sulfocysteine, arginosuccinic acid, hydroxyproline, phosphoethanolamine, sarcosine, carnosine, anserine, 1,3-methyl-histidine, alpha-amino-adipic acid, ethanolamine, gamma-amino-butyric acid, beta-amino-isobutyric acid, L-allo-cystathionine-A, L-cystathionine, cystine, DL-hydroxylysine, DL-allo-hydroxylysine, and homocystine.

19. A method for determining whether a body fluid contains an abnormal level of one or more free amino acids, the method comprising:
   (a) derivatizing free amino acids in the body fluid;
   (b) separating the derivatized free amino acids by liquid chromatography (LC);
   (c) subjecting the separated derivatized free amino acids from step (b) to mass spectroscopic (MS) analysis using a mass spectrometer to identify the amount of derivatized free amino acids from the body fluid by comparing to structurally similar free amino acids from a set of amino acid standards, wherein the identified derivatized free amino acids include one or more free amino acids selected from the group consisting of phosphoserine, sulfocysteine, arginosuccinic acid, hydroxyproline, aspartic acid, phosphoethanolamine, sarcosine, carnosine, anserine, 1,3-methyl-histidine, alpha-amino-adipic acid, beta-alanine, proline, ethanolamine, gamma-amino-butyric acid, beta-amino-isobutyric acid, cysteine, L-allo-cystathionine-A, L-cystathionine, cystine, allo-isoleucine, DL-hydroxylysine, DL-allo-hydroxylysine, and homocystine, wherein said MS is other than tandem MS; and
   (d) comparing the amount of derivatized amino acids from the body fluid to the amount of the same one or more amino acids present in the same body fluid of a healthy individual.

20. The method of claim 19, wherein the set of amino acid standards is added to the body fluid prior to the step involving LC or the step involving MS.

21. The method of claim 19, wherein the free amino acids are derivatized with phenylisothiocyanate.

22. The method of claim 19, further comprising processing the body fluid to obtain an enriched preparation of free amino acids prior to derivatizing the free amino acids.

23. The method of claim 22, wherein the enriched preparation of free amino acids comprises a low molecular weight fraction of the body fluid.

24. The method of claim 19, wherein the body fluid is plasma.

25. The method of claim 19, wherein the set of amino acid standards comprises at least 22 free amino acids.

26. The method of claim 19, wherein the set of amino acid standards comprises at least 30 free amino acids.

27. The method of claim 19, wherein the set of amino acid standards comprises at least 35 free amino acids.

28. The method of claim 19, wherein the set of amino acid standards comprises at least 40 free amino acids.

29. The method of claim 19, wherein the set of amino acid standards comprises at least 45 free amino acids.

30. The method of claim 26, wherein the step involving MS is performed using electrospray ionization.

31. The method of claim 26, wherein the step involving MS is performed using a quadrupole analyzer.

32. The method of claim 26, wherein an abnormal level is indicated when the amount of the one or more derivatized amino acids is higher than the amount of the one or more amino acids present in the same body fluid of a healthy individual.

33. The method of claim 26, wherein an abnormal level is indicated when the amount of the one or more derivatized amino acids is lower than the amount of the one or more amino acids present in the same body fluid of a healthy individual.

34. The method of claim 26, wherein the existence of an abnormal level of an amino acid in the body fluid of an individual is used in the diagnosis of a metabolic disease.

35. The method of claim 26, wherein the identified derivatized free amino acids include one or more free amino acids selected from the group consisting of phosphoserine, sulfocysteine, arginosuccinic acid, hydroxyproline, aspartic acid, phosphoethanolamine, sarcosine, carnosine, anserine, 1,3-methyl-histidine, alpha-amino-adipic acid, beta-alanine, proline, ethanolamine, gamma-amino-butyric acid, beta-amino-isobutyric acid, cysteine, L-allo-cystathionine-A, L-cystathionine, cystine, DL-hydroxylysine, DL-allo-hydroxylysine, and homocystine.

36. The method of claim 26, wherein the identified derivatized free amino acids include one or more free amino acids selected from the group consisting of phosphoserine, sulfocysteine, arginosuccinic acid, hydroxyproline, phosphoethanolamine, sarcosine, carnosine, anserine, 1,3-methyl-histidine, alpha-amino-adipic acid, beta-alanine, proline, ethanolamine, gamma-amino-butyric acid, beta-amino-isobutyric acid, cysteine, L-allo-cystathionine-A, L-cystathionine, cystine, allo-isoleucine, DL-hydroxylysine, DL-allo-hydroxylysine, and homocystine.

37. The method of claim 26, wherein the identified derivatized free amino acids include one or more free amino acids selected from the group consisting of phosphoserine, sulfocysteine, arginosuccinic acid, hydroxyproline, phosphoethanolamine, sarcosine, carnosine, anserine, 1,3-methyl-histidine, alpha-amino-adipic acid, ethanolamine, gamma-amino-butyric acid, beta-amino-isobutyric acid, L-allo-cystathionine-A, L-cystathionine, cystine, allo-isoleucine, DL-hydroxylysine, DL-allo-hydroxylysine, and homocystine.

38. The method of claim 26, wherein the identified derivatized free amino acids include one or more free amino acids selected from the group consisting of phosphoserine, sulfocysteine, arginosuccinic acid, hydroxyproline, phosphoethanolamine, sarcosine, carnosine, anserine, 1,3-methyl-histidine, alpha-amino-adipic acid, ethanolamine, gamma-amino-butyric acid, beta-amino-isobutyric acid, L-allo-cystathionine-A, L-cystathionine, cystine, DL-hydroxylysine, DL-allo-hydroxylysine, and homocystine.

39. The method of claim 1, wherein the identified derivatized free amino acids further include one or more free amino acids selected from the group consisting of arginosuccinic acid, hydroxyproline, aspartic acid, sarcosine, alpha-amino-adipic acid, beta-alanine, proline, ethanolamine, gamma-amino-butyric acid, beta-amino-isobutyric acid, cysteine, L-cystathionine, cystine, allo-isoleucine, DL-hydroxylysine, and homocystine.

40. The method of claim 26, wherein the identified derivatized free amino acids further include one or more free amino acids selected from the group consisting of arginosuccinic acid, hydroxyproline, aspartic acid, sarcosine, alpha-amino-adipic acid, beta-alanine, proline, ethanolamine, gamma-amino-butyric acid, beta-amino-isobutyric acid, cysteine, L-cystathionine, cystine, allo-isoleucine, DL-hydroxylysine, and homocystine.

* * * * *

UNITED STATES PATENT AND TRADEMARK OFFICE
CERTIFICATE OF CORRECTION

| | |
|---|---|
| PATENT NO. | : 7,700,364 B2 |
| APPLICATION NO. | : 10/963442 |
| DATED | : April 20, 2010 |
| INVENTOR(S) | : Scott Goldman |

It is certified that error appears in the above-identified patent and that said Letters Patent is hereby corrected as shown below:

Claim 1, col. 10, line 30, replace "spectroscopic" with --spectrometric--

Claim 19, col. 11, line 52, replace "spectroscopic" with --spectrometric--

Signed and Sealed this

Fourteenth Day of September, 2010

David J. Kappos
*Director of the United States Patent and Trademark Office*